United States Patent [19]

Scheibe et al.

[11] Patent Number: 4,517,287
[45] Date of Patent: May 14, 1985

[54] METHOD AND REAGENT FOR THE ENZYMATIC DETERMINATION OF ENZYME SUBSTRATES

[75] Inventors: Peter Scheibe; Erich Bernt, both of Munich; Sigmar Klose, Berg, all of Fed. Rep. of Germany

[73] Assignee: Boehringer Mannheim GmbH, Mannheim-Waldhof, Fed. Rep. of Germany

[21] Appl. No.: 133,722

[22] Filed: Mar. 25, 1980

[30] Foreign Application Priority Data

Apr. 4, 1979 [DE] Fed. Rep. of Germany ....... 2913553

[51] Int. Cl.$^3$ .................. C12Q 1/00; C12Q 1/50; C12Q 1/62; C12Q 1/28

[52] U.S. Cl. .......................... 435/4; 435/10; 435/11; 435/14; 435/15; 435/16; 435/20; 435/22; 435/26; 435/28

[58] Field of Search ............ 435/14, 4, 10, 11, 20, 435/28, 16, 22, 15, 26

[56] References Cited

U.S. PATENT DOCUMENTS 4,000,042 12/1976 Adams ........................... 435/22
4,241,179 12/1980 Madappally et al. ................ 435/16
4,242,446 12/1980 Madappally et al. ............ 435/16 X Primary Examiner—Robert J. Warden
Attorney, Agent, or Firm—Felfe & Lynch

[57] ABSTRACT

The present invention provides a reagent for the enzymatic determination of an enzyme substrate, containing a system for the determination of the substrate, which comprises at least one enzyme, at least one buffer substance and at least one indicator substance and optionally contains adjuvants, wherein the reagent contains a definite amount of the enzyme substrate in an insufficient amount with regard to the substrate determination capacity of the system for the determination of this substrate.

The present invention also provides a process for the enzymatic determination of an enzyme substrate in the presence of disturbing substances which can react with the substrate itself or with an intermediate or end product of the indicator reaction, wherein, before the addition of the sample to be investigated, a definite amount of the substrate is first reacted with the reagent until reaction is complete, whereafter the sample to be determined is added.

11 Claims, 1 Drawing Figure

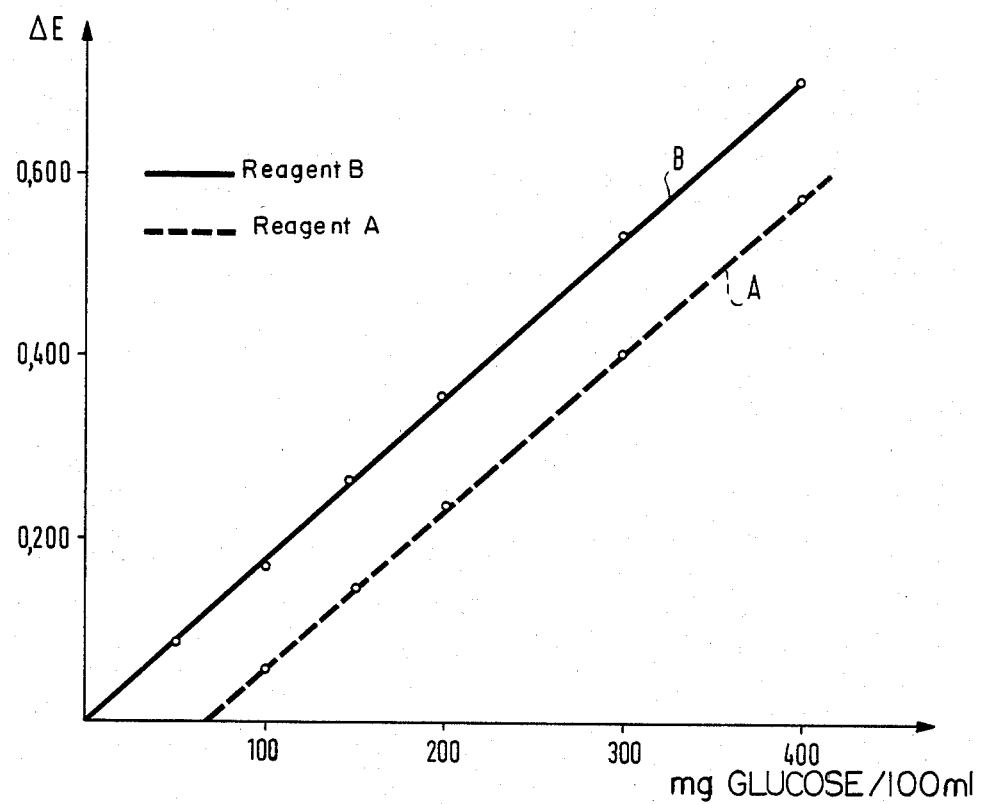

METHOD AND REAGENT FOR THE ENZYMATIC DETERMINATION OF ENZYME SUBSTRATES

The present invention is concerned with a process and reagent for the enzymatic determination of enzyme substrates.

Enzymatic determinations of enzyme substrates, for example of glucose, uric acid and cholesterol, are frequently disturbed by substances contained in the reagents, for example reducing or oxidizing substances, which react with intermediate products or end products of the test system. These disturbing side reactions can be purely chemical or disturbance can take place by participation in the enzyme reaction as competing substrate and the like. In any case, the concentration of the actual indicator product which is measured, for example of a color material formed, is reduced in the case of quantitative and especially of photometric determinations. The proportional relationship between the substrate concentration to be determined and the concentration of the measured indicator product, which is essential for the correctness of the process does not exist in this case. Thus, the amount of substrate determined differs from the amount of substrate acually present. In other words, false results are obtained.

It is an object of the present invention to overcome this problem and to provide a process and a reagent for the enzymatic determination of an enzyme substrate in the presence of disturbing substances which gives correct results and overcomes the above-mentioned difficulties.

According to the present invention, there is provided a process for the enzymatic determination of an enzyme substrate in the presence of disturbing substances which can react with the substrate itself or with an intermediate or end product of the indicator reaction, wherein, before the addition of the sample to be investigated, a definite amount of the substrate is first reacted with the reagent until reaction is complete, whereafter the sample to be determined is added.

By means of the addition of a definite amount of substrate which is always distinctly below the substrate determination capacity of the analysis system, the preliminary reaction is allowed to continue until all the added substrate has been used up. In the course of this preliminary reaction, the disturbing substances are also completely used up. As soon as this reaction has ceased, the actual sample to be investigated, with an unknown content of the substrate to be determined, is then added thereto. The amount of substrate to be determined is then obtained from the difference between the end value of the preliminary reaction for the reaction to be measured and the end value which is obtained after the addition of the sample to be investigated. If desired, it is also possible to perform the actual sample determination kinetically, i.e. instead of measuring the end value, only the rate of reacton is measured.

No general statement can be made regarding the amount of substrate to be added according to the present invention. This amount depends upon the nature of the determination system employed and upon the disturbing substances to be expected. In general, a sufficient excess of substrate will be used with regard to the disturbing substances in order to exclude with certainty the possibility that unreacted disturbing substances are still present when the actual unknown sample is added thereto. On the other hand, too much substrate will also not be added in order not to obtain a blank which is too high for the actual sample reaction and which negatively influences the exactitude of the measurement reaction. The latter plays, for example, a part in the case of photometric measurements of a colored material formed as process product. In the case of such methods depending upon the photometric determination of a colored material appearing as a reaction product, the added definite amount of substrate will be kept so low that disturbing concentrations of colored material are still not formed. This can, in practice, be easily achieved in all cases since such a kind of colored material or other indicator product is at first formed from that amount of substrate which exceeds the amount of substrate necessary for removing the disturbing substances.

In the case of the process according to the present invention, it is not necessary to know the nature of the disturbing foreign substances. Admittedly, these are frequently reducing substances but oxidizing or other disturbing substances are also excluded with certainty by means of the process according to the present invention.

The present invention also provides a reagent for the enzymatic determination of an enzyme substrate, containing a system for the determination of the substrate, which comprises at least one enzyme, at least one buffer substance and at least one indicator substance and optionally contains adjuvants, wherein the reagent contains a definite amount of the enzyme substrate in an insufficient amount with regard to the substrate determination capacity of the system for the determination of this substrate.

When the reagent according to the present invention, present in dry form, is dissolved in water, the reaction for the removal of the disturbing substances already takes place during or after dissolving. The solution thus obtained can be used directly for the actual determination of the enzyme substrate or can again be converted into a dry reagent which is intended for subsequently redissolving before carrying out the determination reaction. However, it is also possible to complete the reagent according to the present invention immediately before use by adding the substrate or, alternatively, by subsequently adding another substance necessary for the start of the reaction, for example, the enzyme or, in the case of a multi-stage reaction with several enzymatic stages, one of the enzymes necessary for the reaction.

According to a preferred embodiment of the reagent according to the present invention, this contains glucose as substrate for the removal of disturbing substances and the system for the determination of the glucose substrate additionally comprises glucose oxidase (GOD), peroxidase (POD), buffer and ABTS [2,2'-azino-di-(3-ethylbenzthiazoline-6-sulphonate)] as color reagent.

In the case of such a reagent, there can be used, referred to 100 ml. of aqueous solution of the substrate determination system, about 750 to 1500 U and preferably 900 to 1200 U of GOD with a specific activity of about 100 U/mg. The corresponding amounts for POD, also with an activity of about 100 U/mg., are 10 to 150 U and preferably 80 to 120 U/100 ml. of reagent solution ready for use. The corresponding concentrations for the ABTS are 75 to 150 mg. and preferably 90 to 120 mg./100 ml. The buffer used has a pH of 6.5 to 7.5 and preferably of 6.8 to b 7.2, the buffer concentration preferably being from 50 to 200 mMol and more preferably from 80 to 120 mMol/liter. The preferred buffer substance is sodium phosphate buffer (disodium hydrogen phosphate/monosodium dihydrogen phosphate) but examples of other buffers which can be used include phosphate-tris buffer, citric acid-tris buffer, tartaric acid-tris buffer and maleic acid-tris buffer, the statements made above again applying with regard to concentration and pH value.

In the case of a reagent of the above-described composition, the amount of glucose is preferably from 0.01 to 0.15 mg. and more preferably from 0.02 to 0.1 mg./100 ml. of solution.

In the case of another preferred reagent according to the present invention for the determination of glucose, the system for the determination of the substrate comprises, in addition to GOD and POD, 4-aminophenazone (PAP) and phenol as color forming components and glucose for the removal of disturbing substances. In this case, the amount of GOD per 100 ml. of reagent solution ready for use is 3000 to 5000 U and preferably 3800 to 4200 U/100 ml., the amount of POD is 50 to 240 U and preferably 160 to 200 U/100 ml. of solution, the amount of PAP is 10 to 20 mg. and preferably 13 to 17 mg./100 ml. and the amount of phenol is 120 to 240 mg. and preferably 160 to 200 mg./100 ml. As buffer, it is, in this case, preferred to use potassium phosphate buffer with the above-given pH value range. The concentration should preferably be from 150 to 250 mMol and more preferably from 180 to 220 mMol/liter. In the case of this reagent, the glucose content is preferably from 0.05 to 0.25 mg. and more preferably from 0.1 to 0.2 mg./100 ml.

The above statements refer to the dissolved reagent but they apply in the same way to the amount of dry reagent intended for the preparation of 100 ml. of solution.

Another preferred reagent according to the present invention contains uric acid as substrate for the removing of disturbing substances and the system for the determination of this substrate comprises uricase, POD, color former and buffer. The color former is preferably a mixture of a 2,4-dichlorophenolate and 4-aminoantipyrine.

In a preferred embodiment, such a reagent contains, per 100 ml. of solution ready for use, 35 to 45 U and preferably 38 to 42 U of uricase with a specific activity of about 9 U/mg. The amount of POD with a specific activity of about 100 U/mg. is preferably 30 to 40 U and more preferably 33 to 37 U/100 ml. of solution. The 2,4-dichlorophenolate, which is used as an alkali metal salt, ammonium salt or amine salt and preferably as the ethylammonium salt, is preferably present in an amount of from 150 to 200 mg. and more preferably of from 165 to 180 mg./100 ml., referred to the ethylammonium salt, these amounts differing, of course, according to the nature of the cation. The 4-aminoantipyrine is preferably used in an amount of from 150 to 250 mg. and more preferably of 180 to 220 mg./100 ml. of reagent.

The buffer substance is preferably one which buffers in the pH range of from 8.5 to 9.5 and more preferably of from 8.7 to 9.3. The buffer concentration is preferably 100 to 200 mMol and more preferably 130 to 180 mMol/liter. Tris-citrate buffer is preferred but other well suited buffer substances include tris-tartaric acid and tris-maleic acid.

In the case of this reagent, the amount of uric acid, in the form of the lithium or sodium salt, is preferably from 0.05 to 0.25 mg. and more preferably from 0.1 to 0.2 mg./100 ml.

Yet another preferred reagent according to the present invention contains cholesterol as substrate for the removing of disturbing substances and the system for the determination of this substrate comprises cholesterol esterase, cholesterol oxidase, POD, colour former and buffer substance. An especially preferred color former is a mixture of 4-aminoantipyrine and phenol.

In a preferred embodiment, this reagent contains, per 100 ml. of solution ready for use, 15 to 25 U and preferably 17 to 23 U of a cholesterol esterase with a specific activity of about 20 U/mg., 20 to 30 U and preferably 22 to 28 U of a cholesterol oxidase with a specific activity of about 25 U/mg., 50 to 200 U and preferably 130 to 180 U of a POD with a specific activity of about 100 U/mg., 15 to 25 mg. and preferably 17 to 23 mg. of 4-aminoantipyrine and 40 to 60 mg. and preferably 45 to 55 mg. of phenol. The buffer used is one with a pH of 7 to 8.5 and preferably of 7.8 to 8.2, with a concentration of from 150 to 250 mMol and preferably of from 180 to 220 mMol/liter. Potassium phosphate buffer is especially preferred but other buffer substances which are able to buffer in the stated range can also be used. The cholesterol content of such a reagent is preferably from 0.20 to 0.60 mg. and more preferably from 0.30 to 0.50 mg./100 ml. of reagent solution or of the amount of dry reagent intended for the preparation of such an amount of reagent solution.

It is to be understood that for the above-described preferred reagent compositions according to the present invention, the given amounts of enzyme only apply for the enzymes of the particular stated specific activity but that they can be replaced by enzyme preparations of other activity.

It can be seen that, according to the present invention, disturbing reactions in the enzymatic determination of enzyme substrates can be removed. This makes it possible to employ less pure reagents, to prolong the period of storage of reagents in which the disturbing substances are first formed and to increase the exactitude of the determinations.

The following Examples are given for the purpose of illustrating the present invention:

EXAMPLE 1

Reagent for the determination of glucose by the ABTS method sodium phosphate buffer (pH 7.0): 100 mMol/l.
glucose oxidase (about 100 U/mg.): 1000 U/100 ml.
peroxidase (about 100 U/mg.): 80 U/100 ml.
ABTS*: 100 mg./100 ml.
glucose: 0.12 mg./100 ml.
*2,2'-azino-di-(3-ethylbenzthiazoline-6-sulphonic acid) diammonium salt.

EXAMPLE 2

Reagent for the determination of glucose by the GOD-PAP method potassium phosphate buffer (pH 7.1): 205 mMol/l.
glucose oxidase (GOD; about 100 U/mg.): 4100 U/100 ml.
peroxidase (POD; about 100 U/mg.): 190 U/100 ml.
PAP (4-aminophenazone): 17 mg./100 ml.
phenol: 200 mg./100 ml.
glucose: 0.2 mg./100 ml.

EXAMPLE 3

Reagent for the determination of cholesterol potassium phosphate buffer (pH 7.9): 200 mMol/l.
cholesterol esterase (about 20 U/mg.): 22 U/100 ml.
cholesterol oxidase (about 25 U/mg.): 24 U/100 ml.
peroxidase (about 100 U/mg.): 150 U/100 ml.
4-aminoantipyrine: 21 mg./100 ml.
phenol: 47 mg./100 ml.
cholesterol: 0.4 mg./100 ml.

EXAMPLE 4

Reagent for the determination of uric acid tris-citrate buffer (pH 9.1): 150 mMol/l.
uricase (about 9 U/mg.): 39 U/100 ml.
peroxidase (about 100 U/mg.): 36 U/100 ml.
2,4-dichlorophenolate, ethylammonium salt: 170 mg./100 ml.
4-aminoantipyrine: 190 mg./100 ml.
uric acid (lithium or sodium salt): 0.16 mg./100 ml.

EXAMPLE 5

Comparative glucose determination

The following procedure was used to demonstrate the improved exactitude of the glucose determination according to the present invention:

Two reagent solutions A and B were prepared by dissolving the reagent according to Example 1 in the necessary amount of water except that, in the case of solution A, the glucose was omitted. For the determination, a standard series of glucose were used containing increasing glucose contents of 50 to 400 mg./100 ml.

Particulars of the determination:
wavelength: Hg 436 nm
cuvette: 1 cm. layer thickness
incubation temperature: 20° to 25° C.

Measurements were made against a blank in a commercially available photometer. The following solutions were pipetted into the cuvettes:

|  | blank | standard | sample |
|---|---|---|---|
| distilled water | 0.1 ml. | — | — |
| diluted standard solution | — | 0.1 ml. | — |
| deproteinised sample | — | — | 0.1 ml. |
| test reagent (A/B) | 5.0 ml. | 5.0 ml. | 5.0 ml. | mixed and incubated at 20° to 25° C. After 25 to 50 minutes, the extinction of the sample ($E_{sample}$) and the extinction of the standard ($E_{standard}$) were measured against the blank. The glucose concentration in the sample is calculated as follows:

$$c = 100 \times \frac{E_{sample}}{E_{standard}} \text{ [mg./100 ml.]}$$

Measurement results:
glucose standard series (50 to 400 mg./100 ml.)

| glucose concentration | extinction in reagent | |
|---|---|---|
|  | A | B |
| 50 mg./100 ml. | — | 0.095 |
| 100 mg./100 ml. | 0.060 | 0.170 |
| 200 mg./100 ml. | 0.236 | 0.353 |
| 300 mg./100 ml. | 0.400 | 0.533 |
| 400 mg./100 ml. | 0.577 | 0.700 |

The above-given measurement results are graphically illustrated in the accompanying drawing. The curve for solution A shows that sample solutions with a glucose content of below about 70 mg./100 ml. cannot be measured because there is no extinction, i.e. no color development. When using a generally employed one-point standard (for example, 100 mg. glucose/100 ml.), in the case of samples with a glucose concentration of from 70 to 100 mg./100 ml. the results obtained were too low in comparison with the actual content, whereas with a glucose content which is above 100 mg./100 ml., the results obtained were too high in comparison with the actual glucose content. Only sample concentrations which correspond exactly to the concentration of the standard give correct measurement values. On the other hand, reagent B according to the present invention always gives correct values.

Results were obtained with human serum samples in the above-described manner and, for comparison, values were also determined by the standard hexokinase method. The results obtained are given in the following Table:

|  | HK/G6P-DH (standard method) | reagent A | reagent B |
|---|---|---|---|
| serum 1 | 53 mg./100 ml. | no measurement value | 51 mg./100 ml. |
| serum 2 | 84 mg./100 ml. | 55 mg./100 ml. | 83.5 mg./100 ml. |
| serum 3 | 135 mg./100 ml. 213 mg./100 ml. | 135 mg./100 ml. |  |

It will be understood that the specification and examples are illustrative, but not limitative of the present invention and that other embodiments within the spirit and scope of the invention will suggest themselves to those skilled in the art.

What is claimed is:

1. In a reagent for the enzymatic determination of an enzyme substrate, containing a substrate determination system including at least one enzyme, at least one buffer substance and at least one indicator substance, the improvement comprising
    including in said reagent a defined amount of the enzyme substrate to be determined, which amount is less than the substrate determination capacity of the said system but is sufficient to react with interfering reagent ingredients.

2. Reagent as claimed in claim 1 wherein the substrate is glucose and said substrate determination system comprises glucose oxidase, peroxidase, ABTS and buffer.

3. Reagent as claimed in claim 1 wherein the substrate is uric acid and said substrate determination system comprises uricase, peroxidase, a 2,4-dichlorophenolate, 4-aminoantipyrine and buffer.

4. Reagent as claimed in claim 1 wherein the substrate is cholesterol and said substrate determination system comprises cholesterol esterase, cholesterol oxidase, peroxidase, 4-aminoantipyrine, phenol and buffer.

5. Reagent as claimed in claim 1 wherein the substrate is glucose and said substrate determination system comprises glucose oxidase, peroxidase, 4-aminophenazone, phenol and buffer.

6. Reagent as claimed in claim 1 also containing at least one adjuvant.

7. Method for the enzymatic determination of an enzyme substrate with a reagent which contains a system for determining the substrate and interfering substances which can react with the substrate or an intermediate or end product of the indicator reaction, which method comprises reacting, before the addition of the sample to be analyzed, a defined amount of the substrate with said reagent until reaction is complete, and then contacting the sample to be determined with said reagent.

8. Method as claimed in claim 7 wherein the enzyme substrate is glucose and the system for determining the substrate comprises glucose oxidase, peroxidase, ABTS and buffer.

9. Method as claimed in claim 7 wherein the substrate is uric acid and the system for determining the substrate comprises uricase, peroxidase, a 2,4-dichlorophenolate, 4-aminoantipyrine and buffer.

10. Method as claimed in claim 7 wherein the substrate is cholesterol and the system for determining the substrate comprises cholesterol esterase, cholesterol oxidase, peroxidase, 4-aminoantipyrine, phenol and buffer.

11. Method as claimed in claim 7 wherein the substrate is glucose and the system for determining the substrate comprises glucose oxidase, peroxidase, 4-aminophenazone, phenol and buffer.

* * * * *